(12) United States Patent
Reiley

(10) Patent No.: US 7,717,920 B2
(45) Date of Patent: *May 18, 2010

(54) ANKLE REPLACEMENT PROSTHESES

(75) Inventor: Mark A Reiley, Piedmont, CA (US)

(73) Assignee: Inbone Technologies, Inc., Boulder, CO (US)

(*) Notice: Subject to any disclaimer, the term of this patent is extended or adjusted under 35 U.S.C. 154(b) by 141 days.

This patent is subject to a terminal disclaimer.

(21) Appl. No.: 11/981,026

(22) Filed: Oct. 31, 2007

(65) Prior Publication Data
US 2008/0065227 A1   Mar. 13, 2008

Related U.S. Application Data

(60) Division of application No. 11/895,721, filed on Aug. 27, 2007, now Pat. No. 7,641,697, which is a division of application No. 11/038,803, filed on Jan. 19, 2005, now Pat. No. 7,314,488, which is a division of application No. 10/699,999, filed on Nov. 3, 2003, now Pat. No. 6,875,236, which is a division of application No. 09/935,479, filed on Aug. 23, 2001, now Pat. No. 6,673,116, which is a continuation-in-part of application No. 09/694,100, filed on Oct. 20, 2000, now Pat. No. 6,663,669.

(60) Provisional application No. 60/160,892, filed on Oct. 22, 1999.

(51) Int. Cl.
*A61B 17/90* (2006.01)
(52) U.S. Cl. ............ 606/96; 606/86 R; 623/21.18
(58) Field of Classification Search .......... 623/21.18; 606/97
See application file for complete search history.

(56) References Cited

U.S. PATENT DOCUMENTS

| 3,839,742 A | 10/1974 | Link |
| 3,886,599 A | 6/1975 | Schlein |
| 4,021,864 A | 5/1977 | Waugh |
| 4,069,518 A | 1/1978 | Groth, Jr. et al. |
| 4,450,591 A | 5/1984 | Rappaport |
| 4,467,801 A | 8/1984 | Whiteside |
| 4,470,158 A | 9/1984 | Pappas et al. |
| 4,474,177 A | 10/1984 | Whiteside |
| 4,840,632 A | 6/1989 | Kampner |

(Continued)

FOREIGN PATENT DOCUMENTS

EP   0 864 305   9/1998

(Continued)

OTHER PUBLICATIONS

G.Lord et al., J.H. Marotte, "Prosthese totale de cheville" Revue de Chirurgie Orthopedique, vol. 59, 1973. pp. 139-151.

(Continued)

*Primary Examiner*—Bruce E Snow
*Assistant Examiner*—Melissa Montano
(74) *Attorney, Agent, or Firm*—Duane Morris LLP

(57) ABSTRACT

A prosthesis is installed in a cavity that traverses a joint between a talus and a calcaneus. The cavity is established by intramedullary guidance with respect to the major axis of the tibia by access through the calcaneus.

5 Claims, 13 Drawing Sheets

U.S. PATENT DOCUMENTS

| | | |
|---|---|---|
| 4,968,316 A | 11/1990 | Hergenroeder |
| 5,207,712 A | 5/1993 | Cohen |
| 5,342,368 A | 8/1994 | Petersen |
| 5,360,450 A | 11/1994 | Giannini |
| 5,766,259 A | 6/1998 | Sammarco |
| 5,866,113 A | 2/1999 | Hendriks et al. |
| 5,947,289 A | 9/1999 | Stridsberg et al. |
| 6,183,519 B1 | 2/2001 | Bonnin et al. |
| 6,197,029 B1 | 3/2001 | Fujimori et al. |
| 6,589,281 B2 | 7/2003 | Hyde, Jr. |
| 6,783,548 B2 | 8/2004 | Hyde, Jr. |
| 6,875,236 B2 | 4/2005 | Reiley |
| 2005/0107791 A1 * | 5/2005 | Manderson ............... 606/62 |
| 2005/0288792 A1 | 12/2005 | Landes et al. |

FOREIGN PATENT DOCUMENTS

| | | |
|---|---|---|
| EP | 1666006 | 7/2006 |
| EP | 1774926 | 4/2007 |
| FR | 2220235 | 10/1974 |
| FR | 2543821 | 10/1984 |
| FR | 2615726 | 12/1988 |
| FR | 2700462 | 1/1993 |
| FR | 2680968 | 12/1993 |
| WO | WO01/30264 | 5/2001 |

OTHER PUBLICATIONS

Database WPI Section PQ, Week 199030, Derwent Publications Ltd. XP-002224011 and SU 1 533 685A (Shadyev B U) Dec. 30, 1989.
PCT ISR for PCT/US2008/080111.

* cited by examiner

FIG. 4
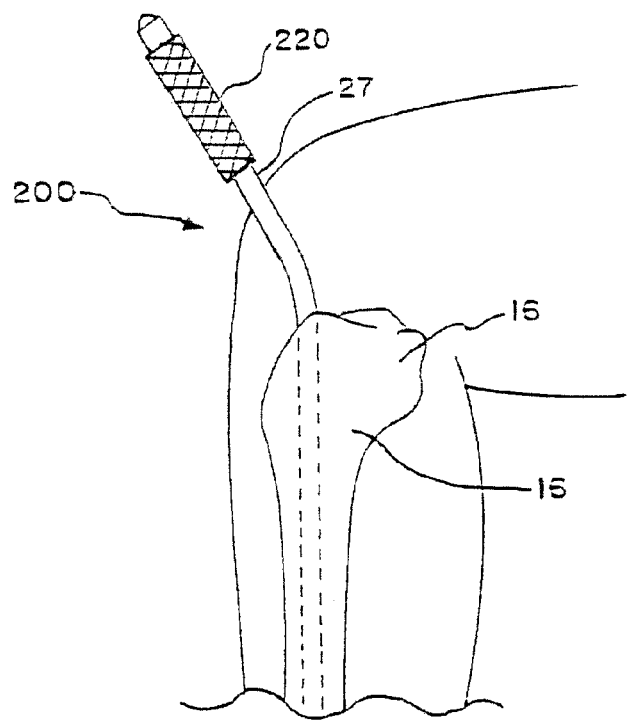
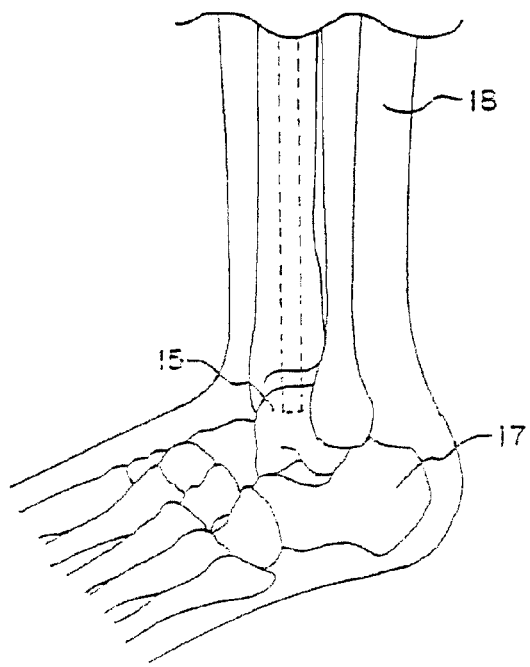

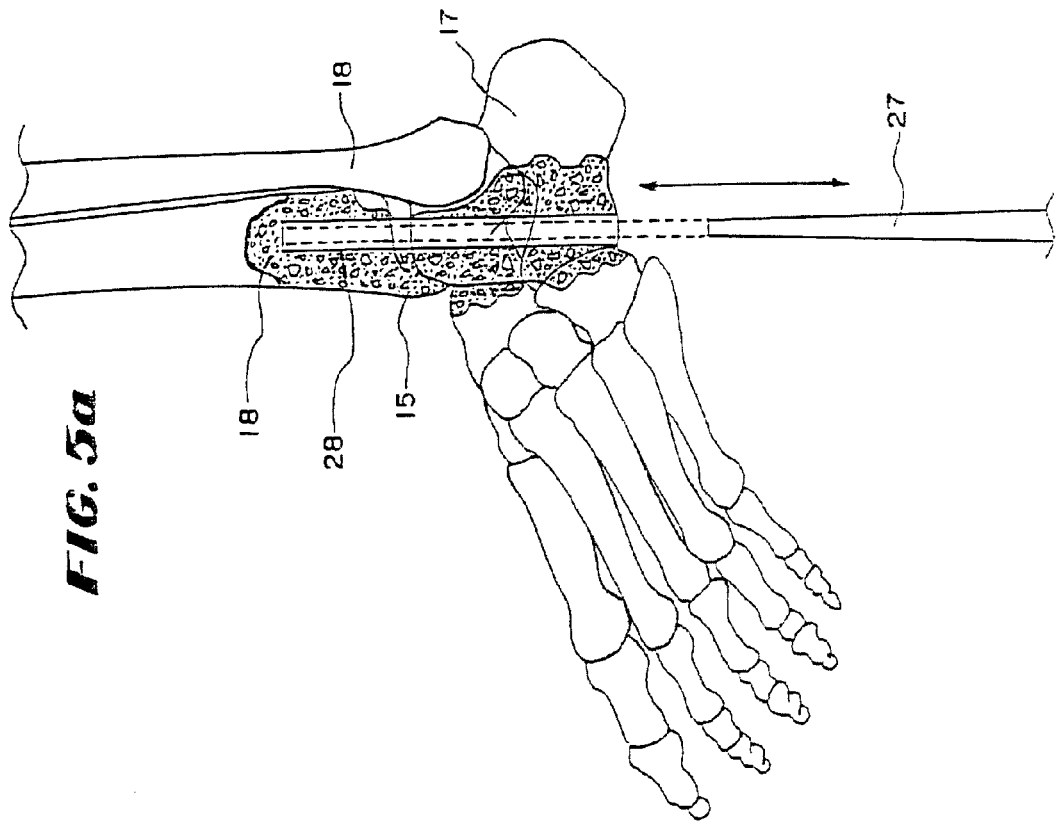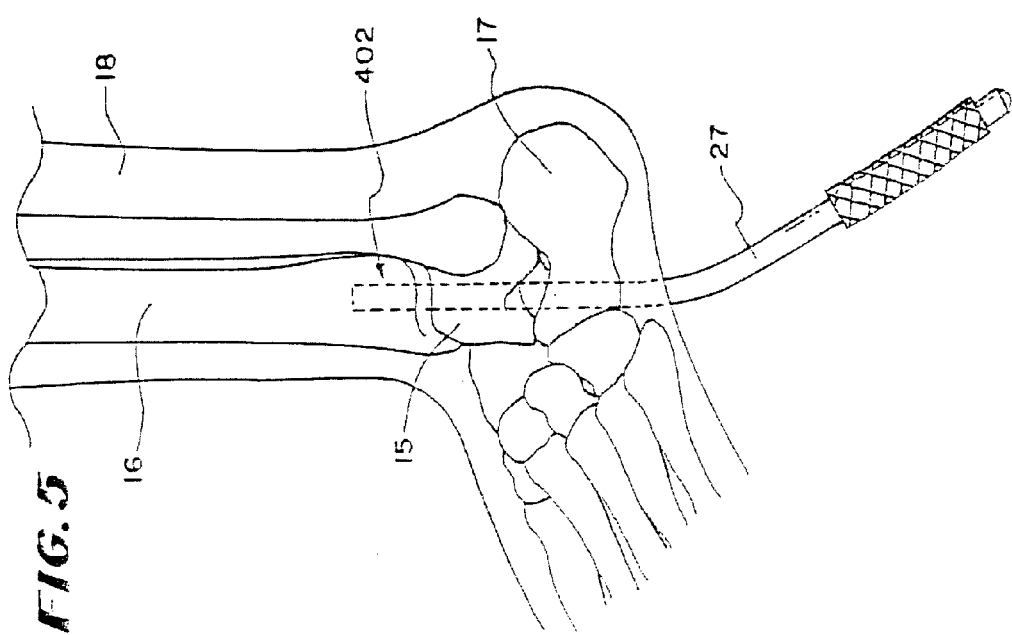

ANKLE REPLACEMENT PROSTHESES

RELATED APPLICATIONS

This application is a division of U.S. patent application Ser. No. 11/895,721, filed Aug. 27, 2007 (now U.S. Pat. No. 7,641,697), which is a division of U.S. patent application Ser. No. 11/038,803, filed Jan. 19, 2005 (now U.S. Pat. No. 7,314,488), which is a division of U.S. patent application Ser. No. 10/699,999, filed Nov. 3, 2003 (now U.S. Pat. No. 6,875,236), which is a division of U.S. patent application Ser. No. 09/935,479, Aug. 23, 2001 (now U.S. Pat. No. 6,673,116), which is a continuation-in-part of U.S. patent application Ser. No. 09/694,100, filed Oct. 20, 2000 (now U.S. Pat. No. 6,663,669), which claims the benefit of U.S. Provisional Patent Application Ser. No. 60/160,892, filed Oct. 22, 1999, all of which are incorporated herein by reference.

FIELD OF THE INVENTION

The invention relates to ankle replacement prostheses, systems, and associated surgical procedures.

BACKGROUND OF THE INVENTION

Until the early to mid 1970's, patients with injured or diseased ankle joints commonly resulting from osteoarthritis (age-related wear of the joints), or rheumatoid arthritis (generalized joint inflammation causing destructive changes), or traumatic arthritis (damage to a joint from a direct injury), had few satisfactory options when their ankle joints failed. Non-surgical options included weight loss, activity modification, medication, injections, braces and therapeutic shoes. The available surgical techniques included ankle arthroscopy (endoscopic examination of the joint), ankle arthrotomy (cutting into the joint to expose the interior) and debridement (opening the joint and removing bone spurs), osteotomy (cutting the bone to realign the joint), ankle fusion (removing the joint and making it stiff), and total ankle arthroplasty (removing the ankle joint and replacing it with an artificial substitute).

Many of the prior art surgical procedures were riddled with problems for the patient. While early success was realized, there was a high long-term term failure rate due to complications such as infection, loosening, and collapse, which lead to additional extensive surgical procedures.

Previous ankle replacement systems typically include a talar member, fixed to the talus, as one of their main functioning components. The talus, however, is relatively small, providing a small area of bone for fixation. Also, in most of these ankle replacement systems, the talar component is cemented to the talus. The combination of fixation with bone cement to a small fixation area allows for erosion of the cement from the fixation area and an increase in compliance due to formation of a soft tissue capsule over time. This contributes to aseptic loosening and migration of the device.

Previous ankle replacement systems are typically installed through incisions made at or near the ankle and make use of extramedullary alignment and guidance techniques. Such surgical procedures require making large incisions at the ankle, moving the tendons and other soft tissue aside, and separating the tibia and fibula from the talus essentially detaching the foot from the leg—to install the device. Such procedures subsequently require complicated extramedullary realignment and reattachment of the foot. These procedures commonly result in infection and extended healing time with possible replacement failure from improper extramedullary realignment. The surgery also has increased risks associated with cutting or damaging neighboring nerves and tendons which may lead to further complications.

There remains a need for a total ankle replacement system that reduces the occurrence of subsidence and aseptic loosening while retaining the majority of the foot's natural motion.

SUMMARY OF THE INVENTION

The invention provides systems and methods for use in ankle arthroplasty which overcomes the problems and disadvantages associated with current strategies and systems in total ankle replacement (TAR).

According to one aspect of the invention, a prosthesis is installed in a cavity that traverses a joint between a talus and a calcaneus. The cavity is established by intramedullary guidance with respect to the major axis of the tibia by access through the calcaneus.

Other objects, advantages, and embodiments of the invention are set forth in part in the description which follows, and in part, will be obvious from this description, or may be learned from the practice of the invention.

DESCRIPTION OF THE DRAWINGS

FIG. 4 is a lateral view of a lower leg and foot demonstrating the intramedullary insertion of a guide pin through the superior part of the tibia and terminating in the talus.

FIG. 5 is a lateral view of a lower leg and foot demonstrating the intramedullary insertion of a guide pin through the plantar surface of the calcaneus, passing through the talus and terminating in the tibia at variable lengths.

FIG. 5a is a sectional view of a foot and depicts the insertion and removal of a guide pin through the plantar surface of the calcaneus, passing through the talus and terminating in the tibia, to produce an intramedullary channel, which may be made of various dimensions by using the guide pin to also direct the course of intramedullary reamers.

DESCRIPTION OF THE INVENTION

I. Anatomy of the Ankle

Figure 1:
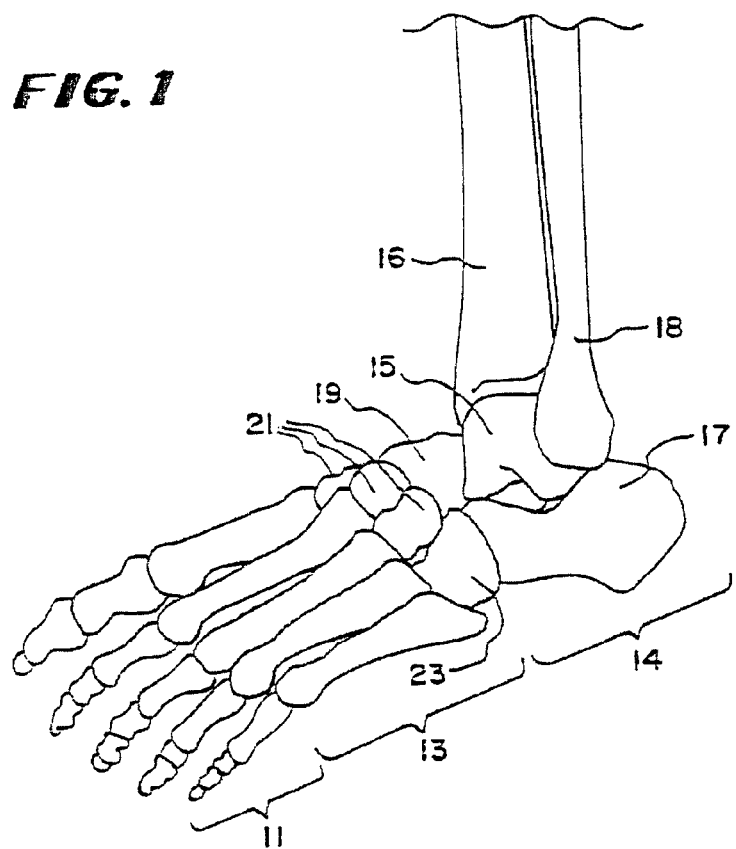
FIG. 1 is a view of the lower leg and foot skeleton.

Referring to FIG. 1, the foot comprises fourteen phalanges or toe bones 11 connected to the metatarsus bones 13. There are also seven tarsal bones 14, of which the talus 15 supports the tibia 16 and the fibula 18, and the heel bone or calcaneus 17. Of the tarsal bones, the talus 15 and the calcaneus 17 are the largest and are adjacent to each other. The other tarsal bones include the navicular 19, three cuneiforms 21, and the cuboid 23.

II. Intramedullary Guidance System

Figure 2:
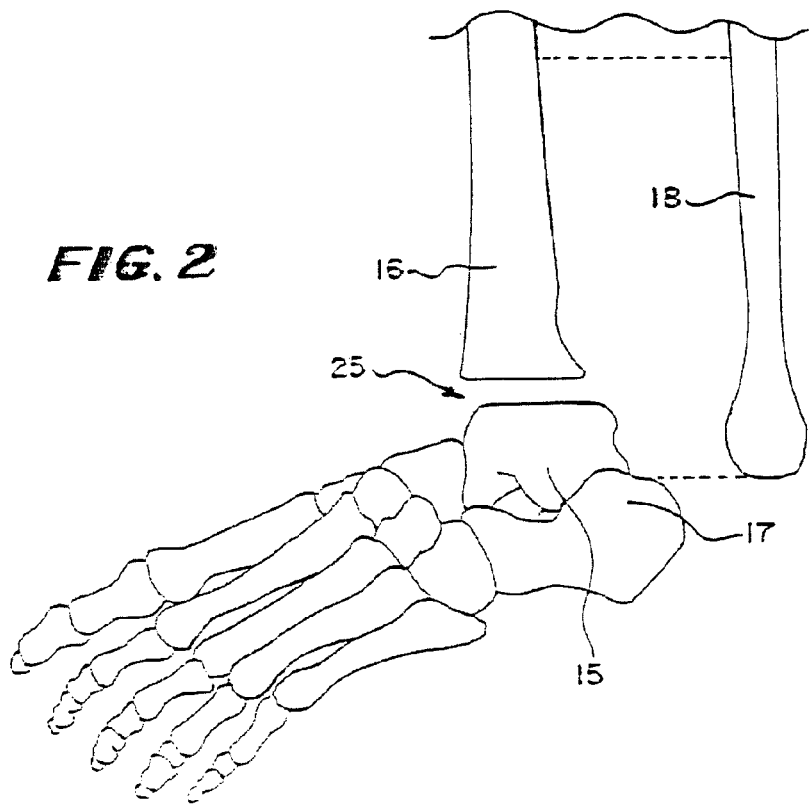
FIG. 2 is a lateral view of a human foot and lower leg skeleton with the fibula shown in an assembly format and having a planarly resected tibia and talus.
Figure 2A:
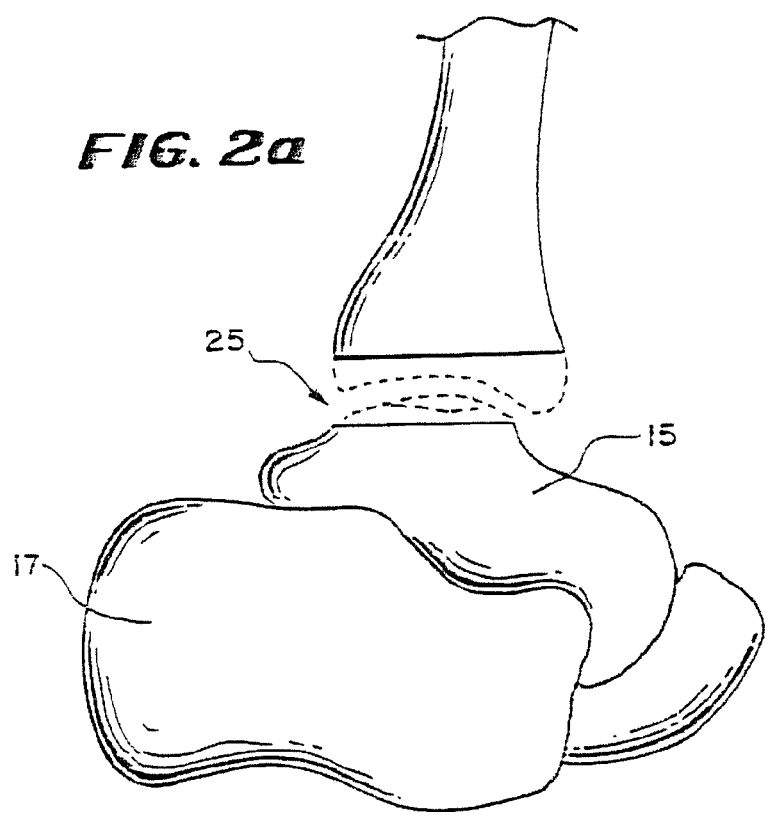
FIG. 2a is a posterior view of a human foot and lower leg skeleton with the fibula not shown and planar cuts of the tibia and talus are depicted.

In performing a total ankle replacement procedure, it is desirable to cut away bone on the inferior end of the tibia 16 and/or the superior end of the talus 15, to thereby form a planar surface or surfaces 25, as FIG. 2 and FIG. 2a shows (in FIG. 2a, the tibia 16 and talus 15 have been resected with the removed portions shown in phantom lines, leaving two planar surfaces 25).

A planar surface increases the amount of bone available for the fixation of a selected prosthetic base. This provides greater stability and less stress absorption. This also decreases the probability of prosthesis loosening and subsidence.

Figure 3:
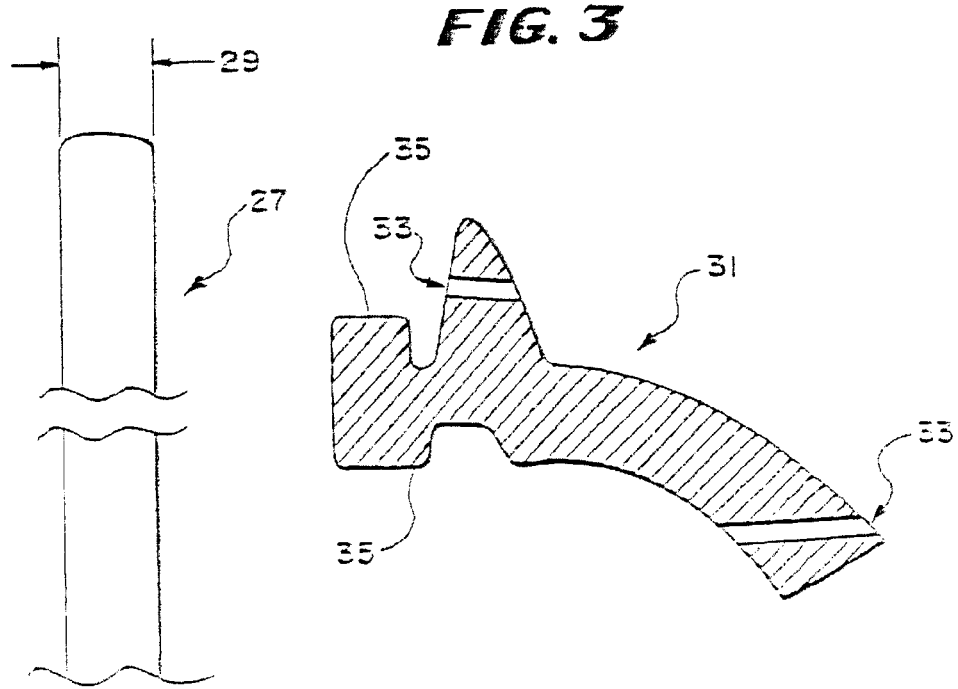
FIG. 3 shows an intramedullary guidance system for providing intramedullary alignment of the tibial and/or talar cuts, one end of the system being oriented toward the tibia and the other end oriented toward the talus.

FIG. 3 shows the components of an intramedullary guidance system 10 for providing a desired alignment of the tibia and talar before and while the tibial and/or talar cuts shown in FIG. 2 are made.

As shown in FIG. 3, the system 10 includes an intramedullary guide pin 27. The intramedullary guide pin 27 is made, e.g., of an inert material used in the surgical arts, such as surgical steel. The guide pin 27 may possess a range of desired diameters 29, depending upon the function or functions it is intended to perform.

For example, the diameter 29 may be relatively small, e.g., about 2 mm to 4 mm, if the pin 27 is to be used principally to form an intramedullary void, as will be described later. The diameter 29 can be made larger, e.g., upwards to about 10 mm, if the pin 27 is to be used to guide passage of a surgical instrument, such as an intramedullary reamer or drill, to form an enlarged intramedullary void, as will also be described later.

In use, the guide pin 27 may be introduced through the tibia (as FIG. 4 shows) or through the calcaneus (as FIG. 5 shows). Before the guide pin 27 is introduced, the foot and ankle are first aligned in an acceptable position. One skilled in the art will recognize that this may require surgically opening the ankle joint to loosen contractures (permanent contraction of muscles, ligaments, tendons) and scarring.

When introduced through the tibia (see FIG. 4), a minimal exposure 200 is made at the tibial tubercle with an awl. Once the exposure has been made, the exposure may be kept open under distraction, pulling of the skin, or any other method common in the surgical arts. Non invasive visualization of the procedure can be accomplished through fluoroscopy or real time MRI, as well as through other means well known to those skilled in the art. Alternatively, or in conjunction with such less invasive means of visualization, open visualization may be used for part and/or all of the procedure.

In this approach, the guide pin 27 passed through the tibia 16, the tibial plafond, and enters the talus.

When introduced through the calcaneus (see FIG. 5), the guide pin 27 is placed retrograde through a minimal exposure in the calcaneus 17. The exposure may be kept open under any method common in the surgical arts and previously discussed. As with the tibial approach, non invasive visualization of the calcaneus approach can be accomplished through fluoroscopy or real time MRI, as well as through other means well known to those skilled in the art. Alternatively, or in conjunction with such less invasive means of visualization, open visualization may be used for part and/or all of the procedure.

In this approach, the guide pin 27 passes through the calcaneus, through the talus 15, through the tibial plafond, and into the tibial shaft.

As FIG. 5a shows, upon removal, the guide pin 27 leaves behind an intramedullary guide void or passage 28 through the region where the tibia adjoins the talus. The passage 28 is sized according to the diameter 29 of the guide pin 27, or with a reamer to an appropriate size consistent with the size of the bones (the calcaneus, the talus, and the tibia).

Figure 7:
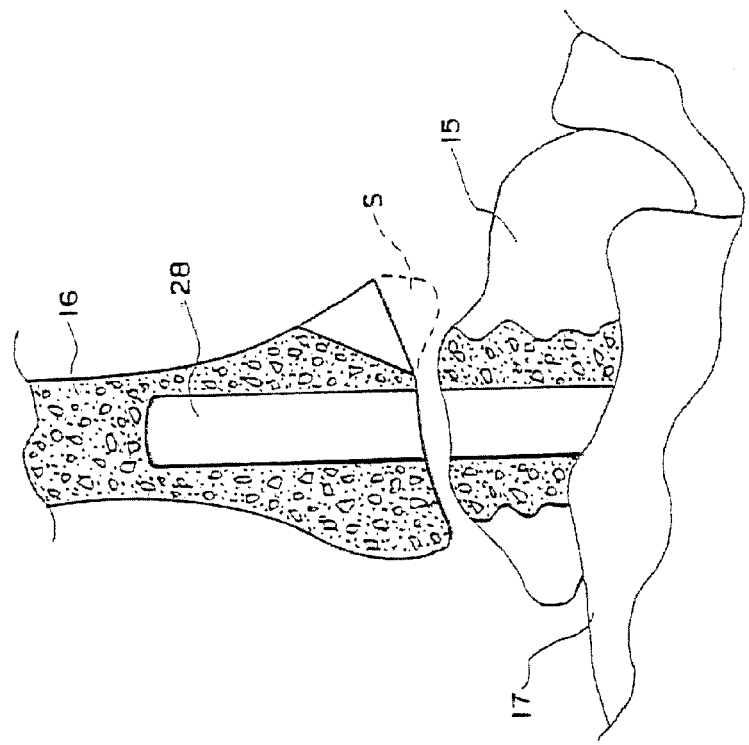
FIG. 7 is a lateral view and partial cross section of the human lower leg and foot showing the intramedullary channel and a resected portion of the anterior lower tibia to allow easier insertion of an intramedullary cutting guide.

As FIG. 7 shows, once the passage 28 is formed, an anterior section S of the tibia 16 can be removed by cutting, to expose the anterior portion of the ankle joint and the guide passage 28.

As shown in FIG. 3, the system 10 also includes an intramedullary cutting guide 31, which is introduced into the ankle through an anterior surgical approach. In use, the intradmedullary cutting guide 31 functions to guide the saw blade used to create the planar surfaces 25 on the tibia and/or talus, as shown in FIG. 2. For this purpose, the cutting guide includes one or more cutting slots 33, through which the saw blade passes. As shown in FIG. 3, the cutting guide 31 also includes an intramedullary locating feature, which in the illustrated embodiment takes the form of an intramedullary locating post 35 (see FIG. 3).

Figure 8:
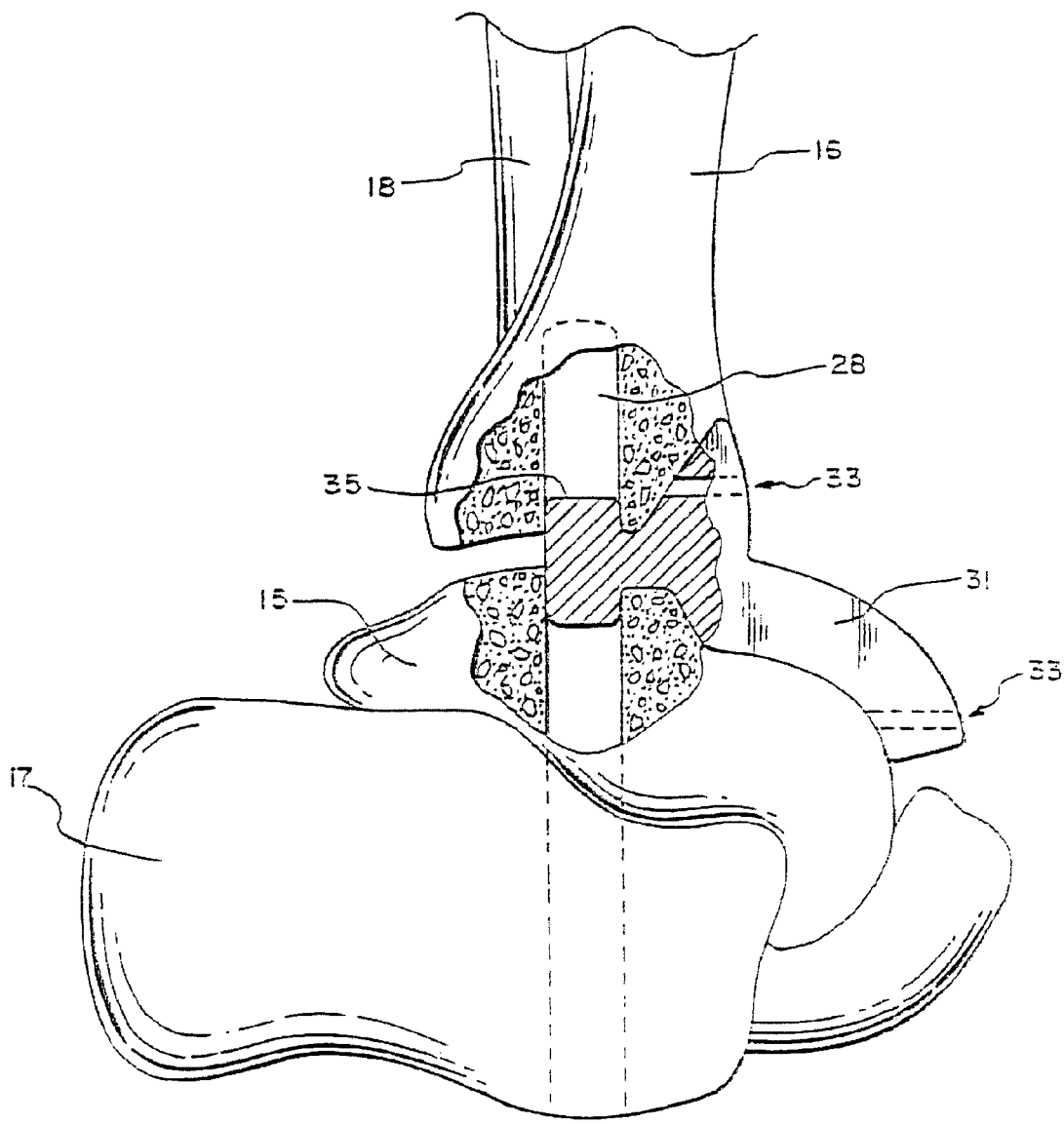
FIG. 8 is a posterior section of the lower leg and foot with the fibula not shown and depicting the insertion of the intramedullary cutting guide between the tibia and the talus.

In use (see FIG. 8), the intramedullary cutting guide 31 may be inserted anteriorly into the ankle joint after the resection of a small amount of bone from the anterior "lip" of the tibia. The alignment post 35 fits into the intramedullary guide passage 28 in both the talus and tibia. The intramedullary post 35 aligns the cutting guide 31 in the desired orientation with the talus 15 and tibia 16. Intramedullary guidance enables the surgeon to produce bony cuts that more closely approximate the mechanical axis of the leg, which extramedullary guides cannot do.

Oriented by the intramedullary post 35, the upper slot 33 of the cutting guide 31 is aligned with the tibial shaft. The lower slot 33 is aligned in the same direction into the dome of the talus. The intramedullary post 35 maintains alignment as a bone saw is passed through the slots 33, across the end regions of talus and tibia. The aligned planar surfaces 25 are thereby formed with intramedullary guidance. Removal of the cutting guide 31 exposes these planar surfaces 25, as FIG. 2 and FIG. 2a show. With intradmedullary guidance, the cuts are superior to cuts using extramedullary guidance. Extramedullary guidance systems rely on surface bony prominences and visualization of the anterior ankle joint. These landmarks are inconsistent and can misdirect bony cuts by the surgeon.

The intramedullary guidance system 10 can be conveniently used with various surgical instruments or prosthetic parts. Because extramedullary alignment is avoided, more precise alignment can be made.

Figure 6:
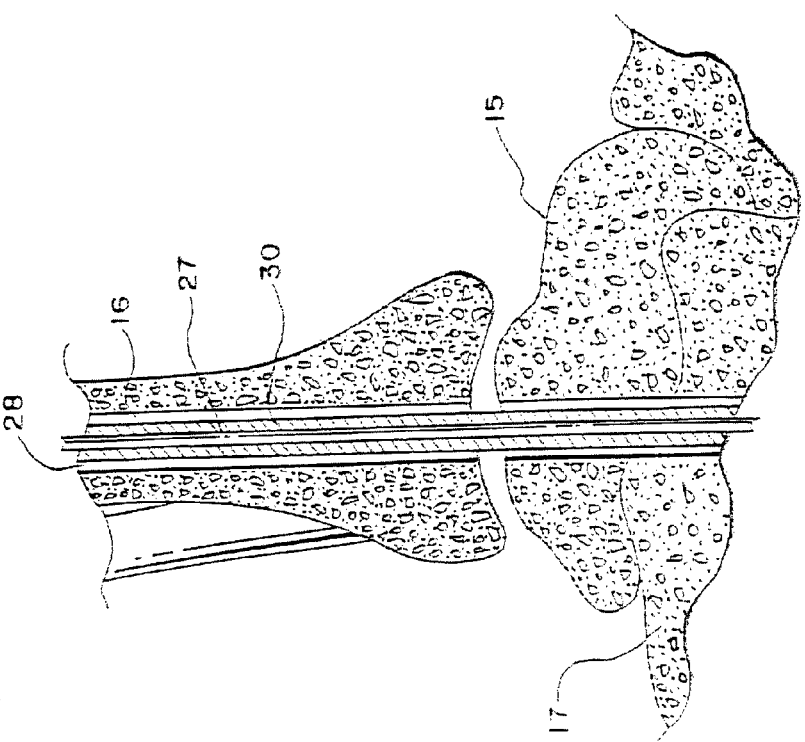
FIG. 6 is a lateral sectional view of the lower leg and foot showing the guide pin surrounded by the reaming instrument creating the intramedullary passage.

For example, as shown in FIG. 6, prior to removal of the guide pin 27 and the use of the cutting guide 31 to form the tibial and talar cuts, the guide pin 27 can serve an additional function, namely, to guide the passage of an intramedullary reaming device or a cannulated drill 30. In this arrangement, the guide pin 27 is used to direct the reaming device 30 over it. A minimally larger exposure will be required on the bottom of the foot to allow the passage of the reaming device or drill bit over the guide pin 27.

Depending upon the manner in which the guide pin 27 is inserted, the reaming device 30 can be guided by the intramedullary guide pin 27, either along a superior path, through the tibia and into the talus (as FIG. 4 shows), or along an inferior path, through the calcaneus and talus and into the tibia (as FIG. 5 shows). Guided by the pin 27, the reaming device 30 leaves behind an enlarged intramedullary void or passage 28.

Alternatively, the guide pin 27 and reaming device 30 may be placed through the tibia or calcaneus simultaneously, or a reaming rod may be placed through the tibia or calcaneus without a guide pin 27, although it is preferable to use a guide pin. The reamer device 30 is preferably 5, 6, 7, 8, 9, or 10 mm wide, depending on the size of the patient's tibia 16.

In this arrangement, the alignment post 35 of the cutting guide 31 is sized to fit into the enlarged reamed intramedullary passage 28. As before described, the post 35 aligns the cutting guide 31 in the desired orientation with the talus and tibia for forming the end cuts, as well maintain the alignment of the reamed intramedullary passage 28.

The size of the alignment post 35 of the cutting guide 31 depends upon how the intramedulary channel is formed. For example, if just a guide pin is used to form the channel, the post 35 will be sized smaller than If an intramedullary reamer is used in forming the channel. If just the guide pin is used to form the channel, straightforward, minimally invasive percutaneous access can be used to insert the guide pin into the calcaneus, into the talus and tibia, thereby forming the relatively small diameter intradmedullary channel.

An upper prosthesis body may be fixed directly to planar cut of the tibia with or without a tibial stem. A lower prosthesis body of the talus may likewise be fixed directly to the planar cut of the talus, or with a fixation stem into the talus or into both the talus and the calcaneus. The upper and lower prosthesis bodies may be used in combination or singly. As will now be described in greater detail later, stemmed upper or lower prostheses may be located on the planar cuts, either individually or in combination.

III. Stemmed Upper Prosthetic Device

Figure 10:
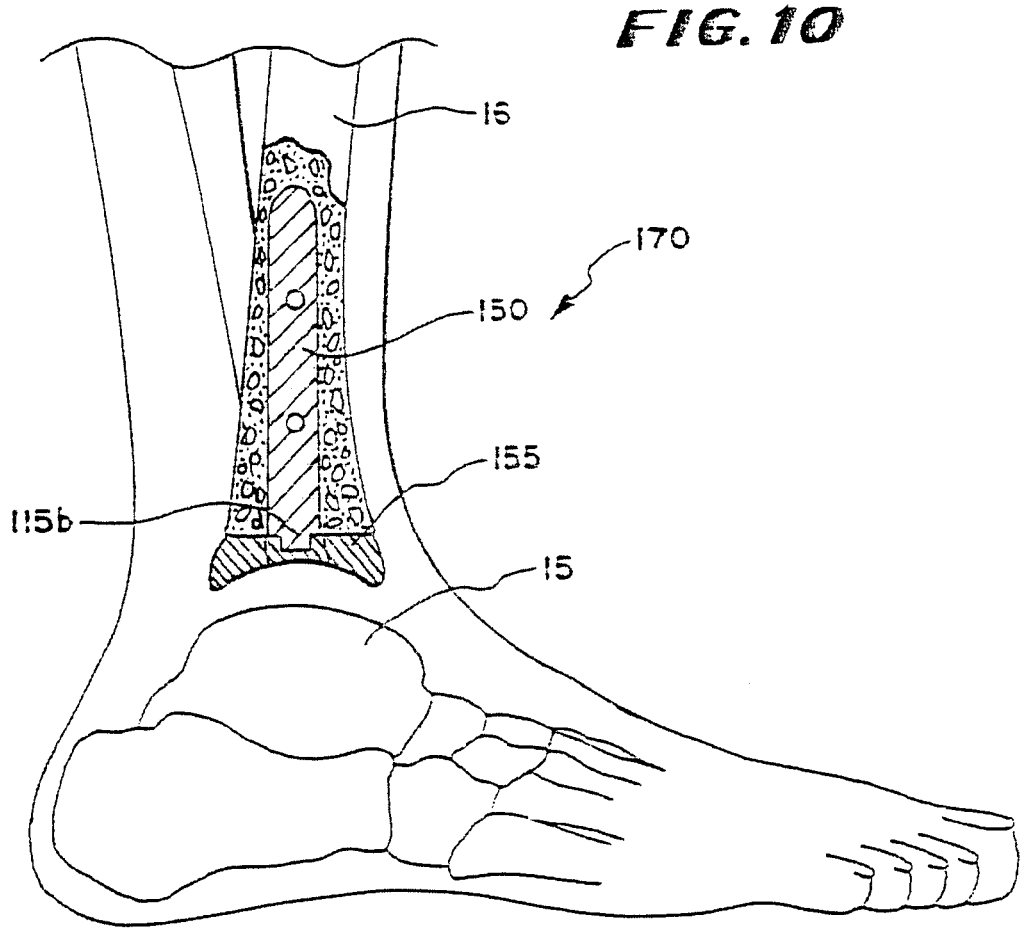
FIG. 10 is a lateral cross-sectional view of the upper prosthetic body, showing the tibial stem and tibial component.

The reamed intramedullary passage 28 formed in the tibia using the intramedullary guidance system 10 can, e.g., serve to accept a stemmed upper prosthetic body 170, as FIG. 10 shows. The stemmed upper prosthetic body can take various forms. Certain representative embodiments are found in U.S. patent application Ser. No. 09/694,100, now U.S. Pat. No. 6,663,669, filed Oct. 20, 2000, entitled "Ankle Replacement System," which is incorporated herein by reference.

In one embodiment (FIG. 10), the upper prosthetic body 170 comprises an elongated tibial stem 150. The tibial stem 150 may be made of any total joint material or materials commonly used in the prosthetic arts, including, but not limited to, metals, ceramics, titanium, titanium alloys, tantalum, chrome cobalt, surgical steel, or any other total joint replacement metal and/or ceramic, bony in-growth surface, sintered glass, artificial bone, any uncemented metal or ceramic surface, or a combination thereof. The tibial stem 150 may further be covered with one or more coatings such as antimicrobial, antithrombotic, and osteoinductive agents, or a combination thereof. These agents may further be carried in a biodegradable carrier material with which the pores of tibial stem 150 may be impregnated. See U.S. Pat. No. 5,947,893.

Figure 10A:
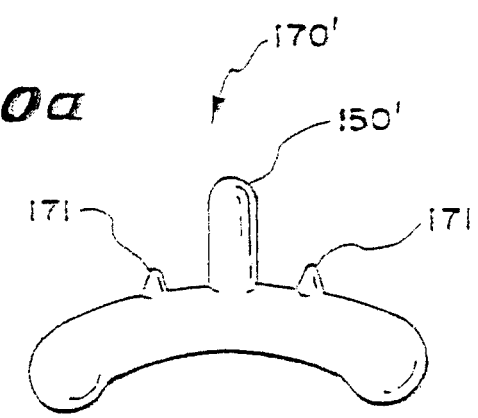
FIG. 10a is a side view of an alternative embodiment of an upper prosthetic body with a shorter tibial stem than shown in FIG. 10.

The tibial stem 150 may be variable lengths, e.g., from 2 cm to 30 cm and variable widths, e.g., from 6 to 12 mm. In the preferred embodiment, the tibial stem 150 is preferably approximately 6 inches in length. Of course, it should be understood that the disclosed tibial stem could be of virtually any length, depending upon the size of the patient, his or her bone dimensions, and the anticipated future mobility of the patient. For example, as FIG. 10a shows, the upper prosthetic body 170' can comprises a shorter tibial stem 150' having a diameter generally the same size (or slightly larger) than the guide pin that forms the passage 28. The body 170' can also include several short, spaced apart derotation pegs 171.

The tibial stem 150 may be inserted into the reamed intramedullary passage 28 either superiorly (through the tibia), or inferiorly (through the calcaneus and talus and into the tibia), depending upon the path along which the guide pin 27 and reaming device 30 have followed.

Figure 11:
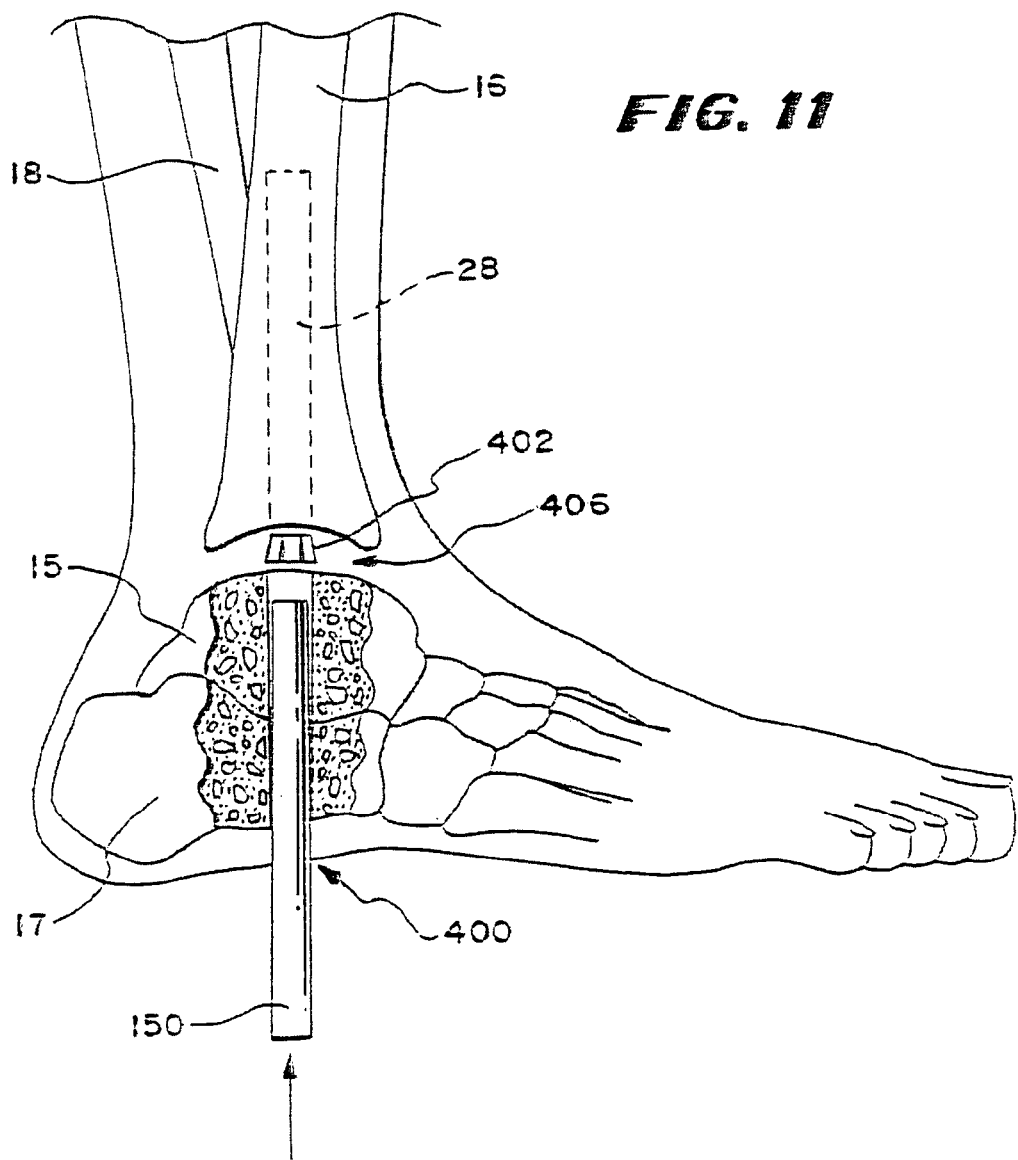
FIG. 11 shows the insertion of a tibial stem through the calcaneus and talus, and (if needed) through an anti-rotational sleeve.
Figure 12:
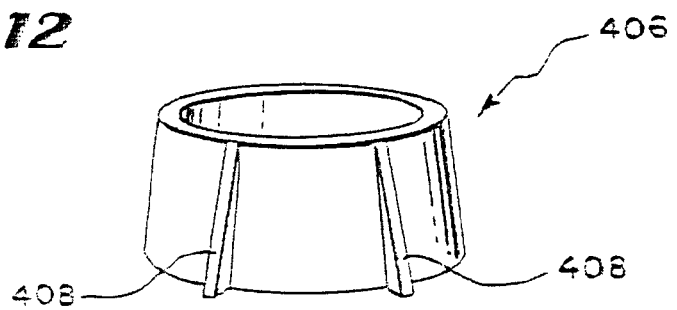
FIG. 12 is a perspective view of the optional anti-rotational sleeve for the tibial stem.

For example, as depicted in FIG. 4, when the passage 28 is made by the pin 27 and reaming device 30 superiorly though the tibia, the tibial stem 150 is inserted in a superior path through the tibia. Alternately, as depicted in FIGS. 11 to 13, when the passage 28 is made by the pin 27 and reaming device 30 retrograde through the calcaneus, the tibial stem 150 may be introduced inferiorly through the retrograde passage 28 through the calcaneus and talus into the tibia (FIG. 11).

Figure 13:
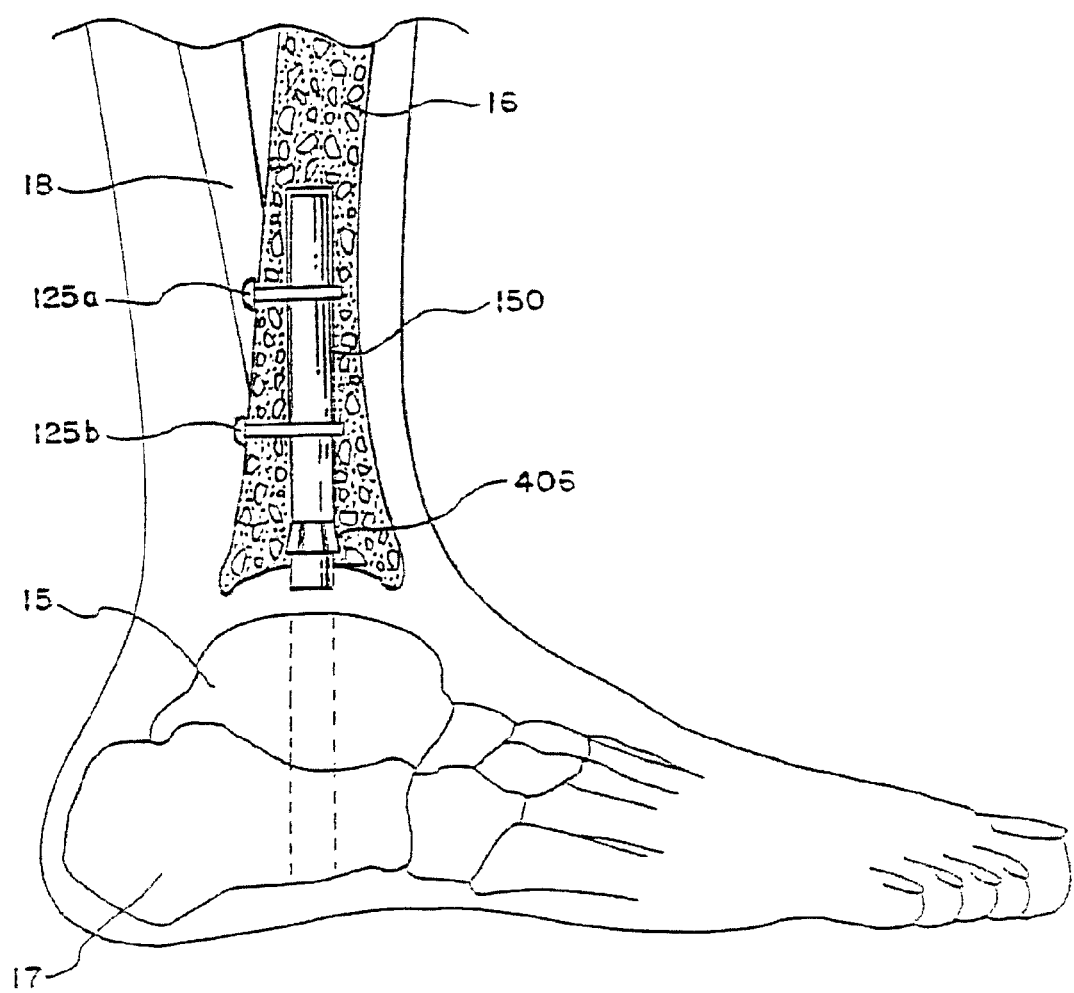
FIG. 13 is a lateral cross sectional view of the tibial stem in the lower tibia and fixed with screws and (optionally) with the anti-rotational sleeve.

The stem 150 is fixed in the lower tibia (FIG. 13). The tibial stem 150 may be fixed in the tibia 16 with poly(methylmethacrylate) bone cement, hydroxyapatite, a ground bone composition, screws, or a combination thereof, or any other fixation materials common to one of skill in the art of prosthetic surgery. An anti-rotational sleeve 406 (see FIG. 12) can also be used alone or in combination with other fixation devices.

In a preferred embodiment, the tibial stem 150 is fixed to the tibia 16 with screws 125a and 125b. If screws are used, they can extend anteriorly, posteriorly, medially, laterally and/or at oblique angles, or any combination thereof.

Optionally, a sleeve 406 (see FIGS. 11 and 12) may be placed about the stem 150, e.g., as the stem is passed between the talus and tibia. The sleeve 406 engages bone along the passage 28. The sleeve 406 imparts an anti-rotational feature, including, e.g., outwardly extending fins. The sleeve 406 may be used in combination with the screws or alone without the screws.

The distal end of the tibial stem 150 may additionally have interlocking components, common to those of skill in the art, at its lower surface to allow other components of the upper prosthesis body to lock into the tibial stem. In a preferred embodiment, the tibial stem 150 has a Morse Taper 115*b* at its lower surface to which a concave dome 155 is attached. The dome 155 can be made of a plastic, ceramic, or metal. The dome 115 articulates with the lower ankle joint surface, which can be the talus bone itself or a lower prosthetic body fixed to the talus, as will now be described.

IV. Stemmed Lower Prosthesis Body

A lower prosthetic body can be supported on the talus, either alone or in association with an upper prosthetic body mounted in the tibia. The upper prosethetic body may be stemmed, as just described, or affixed directly to the tibia without use of a stem. Likewise, the lower prosthetic body may be stemmed or affixed directed to the talus. Certain representative embodiments are found in U.S. patent application Ser. No. 09/694,100, now U.S. Pat. No. 6,663,669, filed Oct. 20, 2000, entitled "Ankle Replacement System," which is incorporated herein by reference.

In one embodiment, the stem for the talar component does not extend beyond the inferior surface of the talar. In another embodiment, a subtalar joint (i.e., the joint formed between talus and calcaneus) is fused to allow fixation of the lower prosthesis body to both the talus and calcaneus. The subtalar joint may be fused using any method common to those of skill in the surgical arts including, but not limited to, fusion with, for example, poly (methylmethacrylate) bone cement, hydroxyapatite, ground bone and marrow composition, plates, and screws, or a combination thereof.

Figure 14:
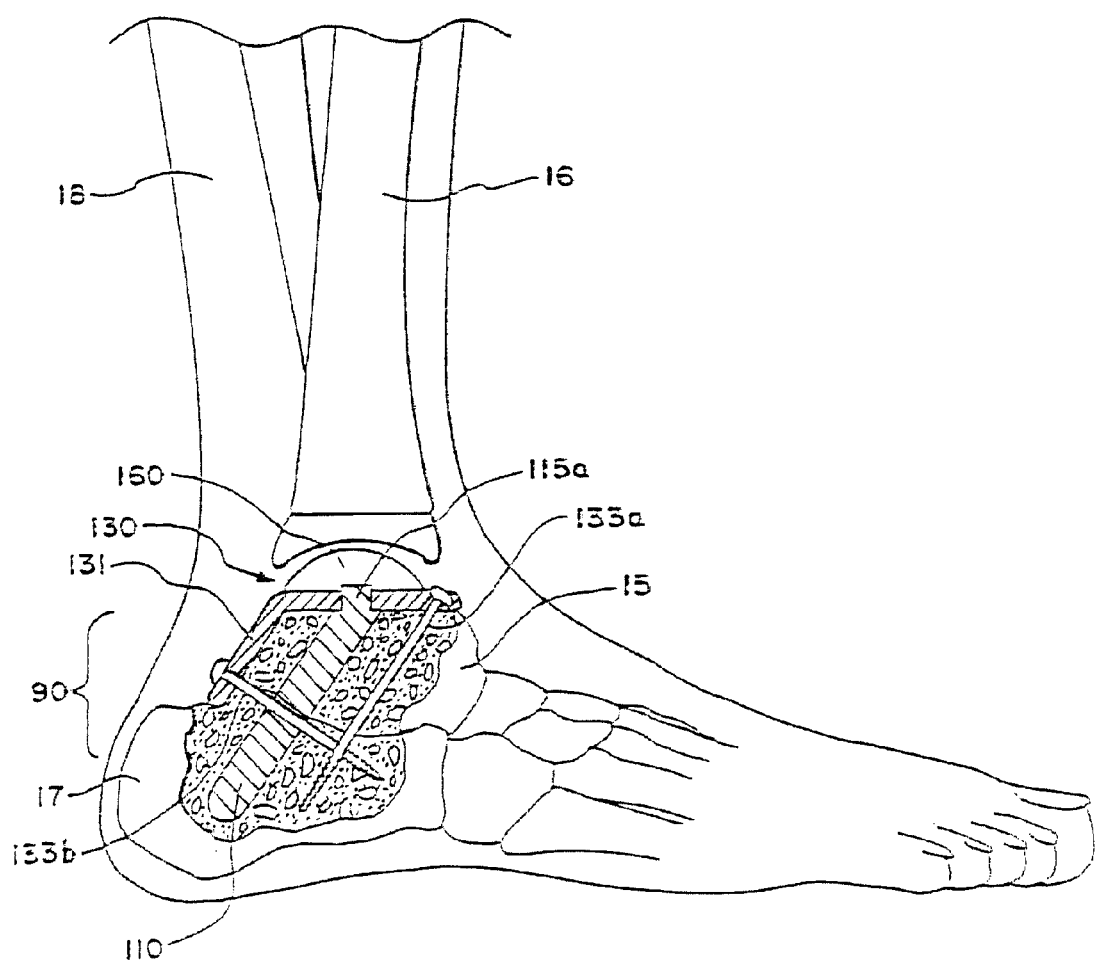
FIG. 14 shows a lateral cross sectional view of a lower prosthetic body in the foot, including the talar component with posterior fixation blade (if needed), talar fixation stem (extending into the calcaneus), and anterior talo-calcaneal fixation screws.
Figure 15:
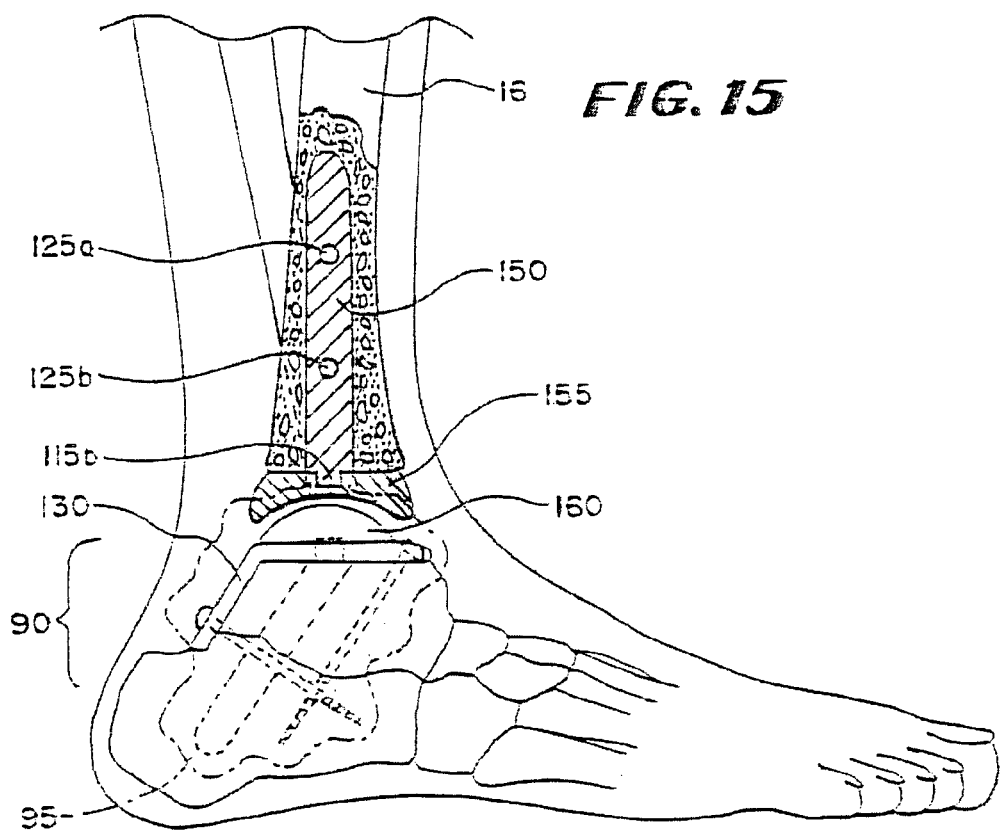
FIG. 15 shows both the upper and lower prosthetic bodies.

FIG. 14 shows one method of fusing the talus 15 to the calcaneus 17 using a stem 110, a plate 130, and screws 133*a*, 133*b*. The talo-calcaneal stem 110 is shown with a Morse Taper 115*a* protruding from the stem 110 and extending beyond the proximal (top) surface of the talus 15. In another embodiment, the Morse Taper could extend down from the talar component into the stem. FIG. 14 also shows an arrangement in which the lower end of the tibia has not been cut and does not carry a prosthesis.

The talo-calcaneal stem 110 may be made of various materials commonly used in the prosthetic arts including, but not limited to, titanium, titanium alloys, tantalum, chrome cobalt, surgical steel, or any other total joint replacement metal and/or ceramic, bony in-growth surface, sintered glass, artificial bone, any uncemented metal or ceramic surface, or a combination thereof. The talo-calcaneal stem 110 may further be covered with various coatings such as antimicrobial, antithrombotic, and osteoinductive agents, or a combination thereof. These agents may further be carried in a biodegradable carrier material with which the pores of the surface of the talo-calcaneal stem 110 may be impregnated. See U.S. Pat. No. 5,947,893, which is incorporated herein by reference. If desired, the talo-calcaneal stem may be coated and/or formed from a material allowing bony in-growth, such as a porous mesh, hydroxyapetite, or other porous surface.

The talo-calcaneal stem 110 may be any size or shape deemed appropriate to fuse the subtalar joint of a patient and is desirably selected by the physician taking into account the morphology and geometry of the site to be treated. For example, the stem 110 may be of variable lengths, from 2 cm to 12 cm, and variable widths, from 4 to 14 mm. In a preferred embodiment, the talo-calcaneal stem 110 is approximately 65 to 75 mm in length and approximately 7 to 10 mm wide. While in the disclosed embodiment the stem 110 has a circular cross-section, it should be understood that the stem could formed in various other cross-sectional geometries, including, but not limited to, elliptical, polygonal, irregular, or some combination thereof. In addition, the stem could be arced to reduce and/or prevent rotation, and could be of constant or varying cross-sectional widths.

The physician is desirably able to select the desired size and/or shape based upon prior analysis of the morphology of the target bone(s) using, for example, plain film x-ray, fluoroscopic x-ray, or MRI or CT scanning. The size and/or shape is selected to optimize support and/or bonding of the stem to the surrounding bone(s).

Figure 9:
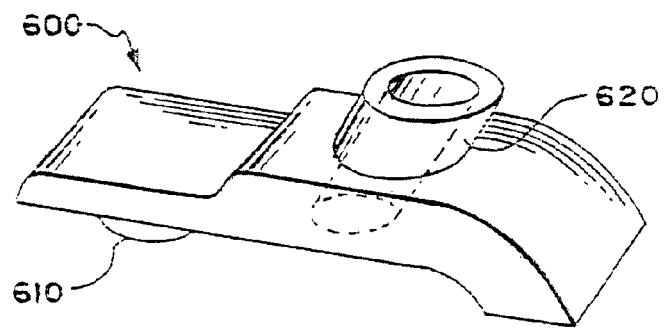
FIG. 9 is a perspective view of a talo-calcaneal reaming jig.
Figure 9A:
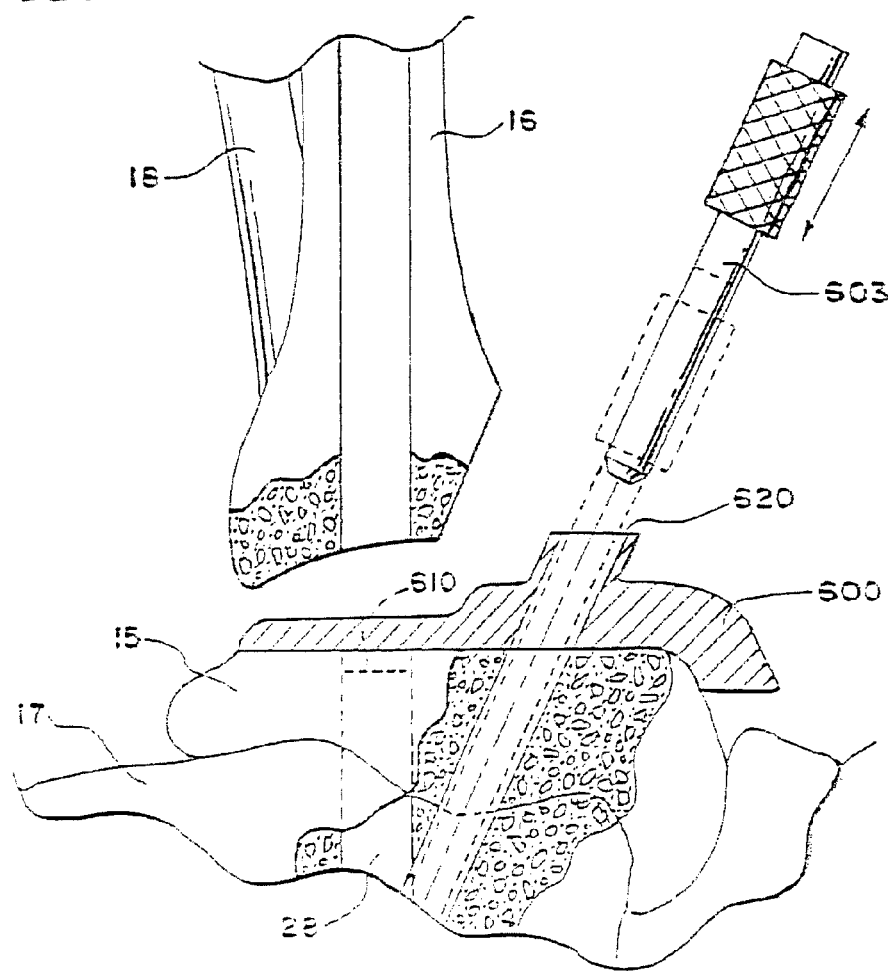
FIG. 9a is a lateral/partial sectional view depicting the insertion of the reaming tool in the talo-calcaneal reaming jig for the posteriorly directed inferior stem to help support the talar component (the drill hole and stem can be only in the talus or extend into the calcaneus for increased stability, and the anterior-posterior position of the talar support stem can be variable).
Figure 9C:
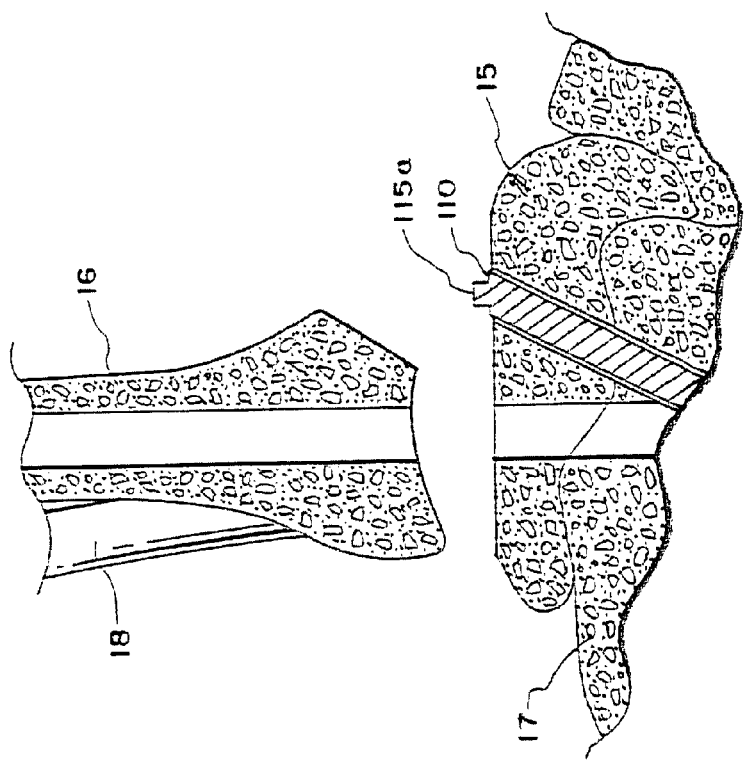
FIG. 9c is a sectional view of resultant channel after the jig is removed, also showing the talar support stem.
Figure 9B:
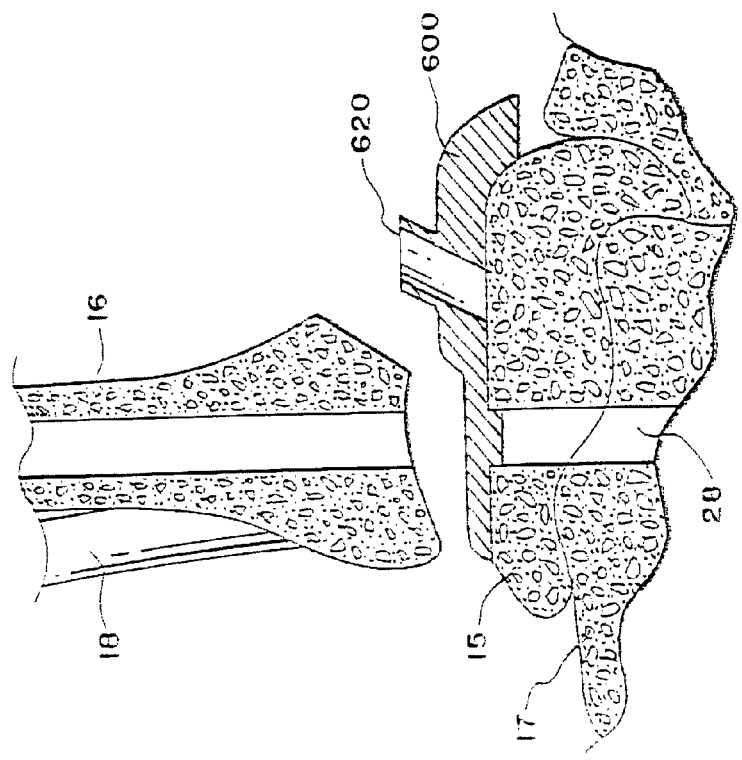
FIG. 9b is a cross-sectional view of the talo-calcaneal jig and channel as positioned on the talus.

As FIGS. 9*a* to 9*c* show, the talo-calcaneal stem 110 can be passed from the top of the talus 15 into the distal calcaneus 17 through a cavity 601 that is drilled through the talus 15 and calcaneus 17. The cavity 601 is preferably drilled after the surface of the talus 15 has cut and flattened, and after the location of the upper prosthesis body.

A suitable jig 600 (see FIG. 9) may be placed in the joint to assist with locating and placing the cavity 601. Certain representative embodiments are found in U.S. patent application Ser. No. 09/694,100, now U.S. Pat. No. 6,663,669, filed Oct. 20, 2000, entitled "Ankle Replacement System," which is incorporated herein by reference. The jig 600 includes a drill guide 620 and a post 610 that, in use, rests in the intramedullary passage 28 (see FIGS. 9*a* and 9*b*). The drill guide 620 can extend from posterior to anterior (as FIG. 9 shows), or alternatively, from anterior to posterior.

The drill bit 603 for the jig 600 (see FIG. 9*a*) is preferably about ½ mm wider than the width of the talo-calcaneal stem 110. The talo-calcaneal stem 110 may be further adapted so that the talo-calcaneal stem 110 is inserted as the cavity is being drilled or so that the talo-calcaneal stem itself is used to drill the hole.

Once the cavity 601 is formed, any easily accessed cartilage from the talo-calcaneal joint may be scraped, e.g., using a small angled curet or any other instrument commonly used in the surgical arts. The subtalar joint can then be fused by passing a talo-calcaneal stem 110 down the cavity 601. The cavity 601 may be partially filled with a bone cement prior to the installation of the talo-calcaneal stem 110 to help fix the talo-calcaneal stem 110 to the subtalar joint. Desirably, the stem 110 incorporates screw holes or other openings to accommodate interlocking hardware, such as screws, to increase fixation and minimize rotation.

The stem 110 desirably includes a Morse Taper 115*a*. A cap 160*a* fits on the Morse Taper 115*a* to form an articulating joint surface with the upper prosthesis. The upper surface of the cap 160 can be designed to fit the particular needs and walking requirements anticipated by the physician and patient. For example, a low demand surface, such as for an individual of advanced years having a less-active lifestyle, could comprise a simple smooth arc, without the "peaks and valleys" of the talus 15 that run from anterior to posterior. In addition, a low demand surface may not require a difference in the anterior to posterior talar width, which in an adult male can be approximately 4 to 5 mm wider in its anterior portion than its posterior portion. A higher demand surface, for a more active individual, may incorporate the trochlea (valley) in the talus as well as various other anatomical features found on the talus.

Figure 16:
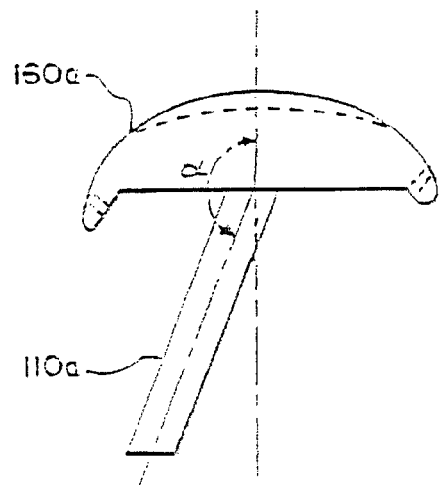
FIG. 16 shows an alternative lower prosthetic unit, with talar fixation stem at various angles.
Figure 17:
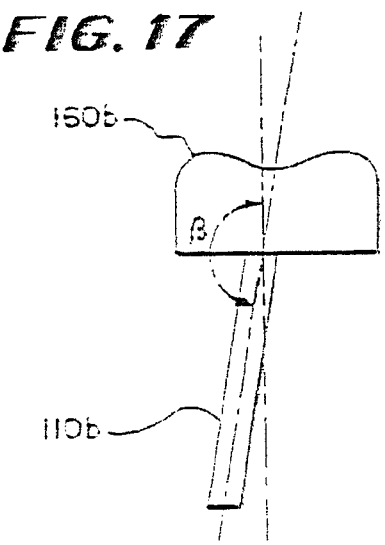
FIG. 17 shows another alternative lower prosthetic unit, with talar fixation stem at various angles.

Desirably, as best seen in FIG. 16, the stem 110*a* extends downward from the cap 160*a*, forming an angle $\alpha$ relative to the vertical axis—taken relative to the longitudinal axis of cap 160a (front to rear of the foot). In one embodiment, the angle α will range from 105° to 205°, depending upon the size and orientation of the calcaneus 17 as well as the position of the lower prosthesis body. Moreover, as best seen in FIG. 17, the stem may form an angle β relative to the vertical axis—taken relative to the transverse axis of the cap 160b (medial to lateral side of the foot). In a preferred embodiment, the angle β will range from 155° (on the medial side of the foot) to 240° (on the lateral side of the foot), depending upon the size and orientation of the calcaneus 17 as well as the position of the lower prosthesis body. Desirably, the lower portion of the stem of the implant will not extend outside of the calcaneus.

As shown in FIG. 14, a plate 130 may be fixed to the top of the talus 15. The plate 130 can have an overhang portion 131 which allows the plate 130 to overlap both the talus 15 and part of the calcaneus 17. The plate 130 and overhang portion 131 may be made of various materials commonly used in the prosthetic arts including, but not limited to, polyethylene, biologic type polymers, hydroxyapetite, rubber, titanium, titanium alloys, tantalum, chrome cobalt, surgical steel, or any other total joint replacement metal and/or ceramic, bony in-growth surface, sintered glass, artificial bone, any porous metal coat, metal meshes and trabeculations, metal screens, uncemented metal or ceramic surface, other bio-compatible materials, or any combination thereof. The plate 130 and overhang portion 131 may further be covered with various coatings such as antimicrobial, antithrombogenic, and osteoinductive agents, or a combination thereof. See U.S. Pat. No. 5,866,113 to Hendriks, et al, incorporated herein by reference. These agents may further be carried in a biodegradable carrier material with which the pores of the plate 130 and overhang portion 131 may be impregnated. In one preferred embodiment, the tray comprises a metal-backed polyethylene component.

The plate 130 and/or the overhang portion 131 may be fixed to the subtalar joint 90 with poly(methylmethacrylate) bone cement, hydroxyapatite, a ground bone and marrow composition, screws, or a combination thereof, or any other fixation materials common to one of skill in the art of joint replacement surgery. In a preferred embodiment, the plate 130 and overhang portion 131 are fitted over the Morse Taper 115a of the talo-calcaneal stem 110 and fixed to the talus 15 and calcaneus 17 with screws 133a and 133b. In another embodiment, the posterior overhang portion 131 can be eliminated.

The lower prosthesis body may be formed in a single unit or, as illustrated, as a multi-component prosthesis.

In other embodiments, the upper prosthesis body may additionally comprise a fibular prosthesis of any variety known in the art of joint replacement. The fibular prosthesis would replace the inferior end of the fibula, especially when this prosthesis is used to revise a total ankle replacement system that has removed the distal end of the fibula. In still further embodiments, either the lower prosthesis body, upper prosthesis body, or both, as described above, may be fixed into strengthened or fortified bone. The bones of the subtalar joint, tibia, or fibula may be strengthened prior to or during fixation of the prosthesis using the methods described in U.S. Pat. No. 5,827,289 to Reiley. This type of bone strengthening procedure is particularly suggested for osteoporotic patients who wish to have a total ankle replacement.

It should be appreciated that installed prosthetic system need not include a calcaneal stem. Thus, the system would only include the tibial stem, the tibial component and the talar component. In this case there would be not Morse Taper holes or stems on the under surface of the talar component, just a flat or minimally stem component with or without screw holes for screw fixation.

Likewise, the installed prosthetic system need not include a tibial stem component. In this case, the system would include the tibial component without the Morse Taper attachments on its superior surface, the talar component, and the calcaneal stem component.

Furthermore, the installed prosthetic system need not include any stemmed component being utilized. However, the intramedullary guidance system 10, deployed either superiorly from the tibia, or inferiorly from the calcaneus, would still provide intramedullary alignment of the tibial and talar cuts. In this arrangement, the tibial component and the talar component would be utilized, without Morse Taper stems or holes on either implant, but the intramedullary guidance system would still be used to insure properly aligned cuts in the talus and tibia.

It should be understood that the devices and methods of the present invention could be used as an index (initial) total ankle replacement, as well as a revision ankle replacement. If used as a revision device, only a portion of the disclosed methods and devices may be necessary in conjunction with such a procedure.

Other embodiments and uses of the inventions described herein will be apparent to those skilled in the art from consideration of the specification and practice of the inventions disclosed. All documents referenced herein are specifically and entirely incorporated by reference. The specification should be considered exemplary only with the true scope and spirit of the invention indicated by the following claims. As will be easily understood by those of ordinary skill in the art, variations and modifications of each of the disclosed embodiments can be easily made within the scope of this invention as defined by the following claims.

I claim:

1. A system for providing intramedullary guidance to install an ankle prosthesis, comprising:
   an intramedullary guide pin having a length and a diameter, the length of the intramedullary guide pin being sufficient to extend from a tibial tubercle through a talus into a calcaneus, the diameter of the intramedullary guide pin being sufficient to be received within the tibia; and
   a cutting guide having an alignment post and defining first and second slots, the alignment post sized and configured to be received in a passage formed in the talus and the tibia by the intramedullary guide pin, the first and second slots being defined in the cutting guide in a substantially parallel, spaced relationship to one another.

2. The system of claim 1, wherein the alignment post extends in a substantially perpendicular direction with respect to the directions in which the first and second slots extend.

3. The system of claim 1, wherein the first slot is located on the cutting guide such that it provides a guide for cutting the tibia when the cutting guide is disposed within the passage formed in the talus and the tibia.

4. The system of claim 1, wherein the second slot is located on the cutting guide such that it provides a guide for cutting the talus when the cutting guide is disposed within the passage formed in the talus and the tibia.

5. The system of claim 1, wherein the intramedullary guide pin is sized and configured to guide one of an intramedullary reaming device or a cannulated drill when disposed in the calcaneus, talus, and tibia.

* * * * *